United States Patent [19]

Dittrich et al.

[11] 4,098,900
[45] Jul. 4, 1978

[54] N,N'-DIPHENYL-GUANIDINE DERIVATIVES

[75] Inventors: Volker Dittrich, Zeiningen; Werner Töpfl, Dornach; Odd Kristiansen, Möhlin, all of Switzerland

[73] Assignee: Ciba-Geigy Corporation, Ardsley, N.Y.

[21] Appl. No.: 663,414

[22] Filed: Mar. 3, 1976

[30] Foreign Application Priority Data

Mar. 10, 1975 [CH] Switzerland ............. 3028/75
Feb. 4, 1976 [CH] Switzerland ............. 1357/76

[51] Int. Cl.² ............... C07C 143/75; C07C 143/79; A61K 31/18
[52] U.S. Cl. .................... 424/304; 260/556 A; 260/556 AR; 260/556B; 424/309; 424/321; 560/12
[58] Field of Search ............. 260/465 C, 465 D, 470, 260/556 A, 556 AR, 565, 556 B; 424/304, 309, 321

[56] References Cited

U.S. PATENT DOCUMENTS 3,068,236  12/1962  Krepcho ................ 260/556 AR X
3,694,504   9/1972  Danielewicz et al. ...... 260/556 AR
3,714,247   1/1973  Dixon ..................... 260/556 AR

FOREIGN PATENT DOCUMENTS 1,311,913  3/1973  United Kingdom.

OTHER PUBLICATIONS

Burmistrov et al., CA 68:68719a (1968).

Primary Examiner—Robert V. Hines
Assistant Examiner—Thomas A. Waltz
Attorney, Agent, or Firm—Harry Falber

[57] ABSTRACT

N,N'-Diphenyl-guanidine derivative of the formula

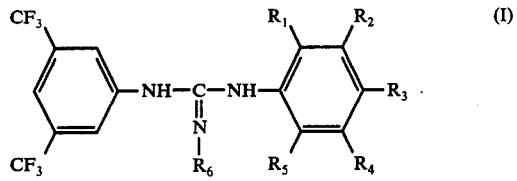

wherein $R_1$, $R_2$, $R_3$, $R_4$ and $R_5$ each represent hydrogen, halogen, $C_1$-$C_5$ alkyl, $C_1$-$C_5$-halogenalkyl, $C_1$-$C_5$-alkoxy, ($C_1$-$C_5$-alkyl)-carbonyl, ($C_1$-$C_5$-alkoxy)-carbonyl, cyano and/or nitro and $R_6$ represents $C_1$-$C_5$-alkylsulfonyl or optionally substituted phenylsulphonyl, processes for their production, and their use in pest control.

8 Claims, No Drawings

N,N'-DIPHENYL-GUANIDINE DERIVATIVES

The present invention relates to N,N'-diphenyl-guanidine derivatives, to processes for their production, and to their use in pest control.

The said N,N'-diphenyl-guanidine derivatives have the formula

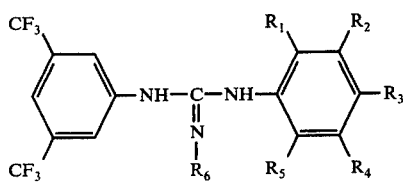

wherein $R_1$, $R_2$, $R_3$, $R_4$ and $R_5$ each represent hydrogen, halogen, $C_1$-$C_5$-alkyl, $C_1$-$C_5$-halogenoalkyl, $C_1$-$C_5$-alkoxy, ($C_1$-$C_5$-alkyl)-carbonyl, ($C_1$-$C_5$-alkoxy)-carbonyl, cyano and/or nitro, and $R_6$ represents $C_1$-$C_5$-alkylsulphonyl or optionally substituted phenylsulphonyl.

By haolgen are meant fluorine, chlorine, bromine and iodine, especially chlorine and bromine.

The alkyl or alkoxy groups denoted by $R_1$ to $R_6$ can be straight-chain or branched-chain. Examples of such groups are, inter alia: methyl, methoxy, ethyl, ethoxy, propyl, isopropyl, n-, i-, sec.- and tert.-butyl, n-pentyl and isomers thereof.

Substituents on the phenyl ring of the phenylsulphone group in the case of $R_6$ are, for example: halogen, $C_1$-$C_5$-alkyl, $C_1$-$C_5$-alkoxy, trifluoromethyl, nitro, amino and/or cyano.

Compounds of the formula I which are of particular importance on account of their action are those wherein $R_1$, $R_2$, $R_3$, $R_4$ and $R_5$ each represent hydrogen, chlorine and/or trifluoromethyl, and $R_6$ represents methylsulphonyl, ethylsulphonyl or 4-chlorophenylsulphonyl.

The compounds of the formula I can be produced by methods known per se; they can for example be produced as follows:

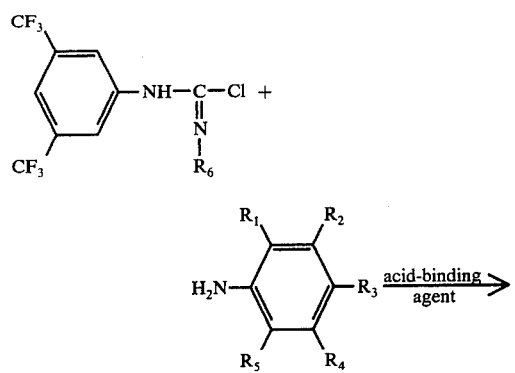

Alternately, the $CF_3$ groups and the $R_1$ – $R_5$ groups may be interchanged in the respective phenyl rings such that the above equation would read as follows:

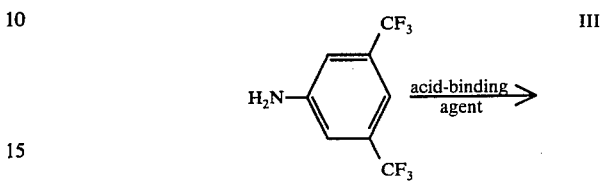

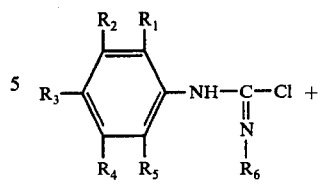

In the formulae II and III, the symbols $R_1$ to $R_6$ have the meanings given for formula I. Suitable acid-binding agents are, for example, the following bases: tertiary amines such as triethylamine, dimethylaniline or pyridine; inorganic bases such as hydroxides and carbonates of alkali metals and alkaline-earth metals, preferably sodium carbonate and potassium carbonate.

The process is performed at a reaction temperature of $-10$ to $+100°$ C, preferably at 20 to 80° C, under normal or elevated pressure and in a solvent or diluent.

Suitable solvents and diluents are, e.g., ethers and ethereal compounds, such as diethyl ether, dipropyl ether, dioxane, dimethyloxyethane or tetrahydrofuran; amides such as N,N-dialkylated carboxylic acid amides; aliphatic, aromatic as well as halogenated hydrocarbons, particularly benzene, toluene, xylenes, chloroform and chlorobenzene; nitriles such as acetonitrile; dimethylsulphate; ketones such as acetone and methyl ethyl ketone. The starting materials of the formulae II and III are known and can be produced in a manner analogous to that in the case of known processes. There is thus described, for example, in J. Chem. Soc. 4063 (1952) a process for the production of compounds of the formula III.

The compounds of the formula I can exist in the following tautomeric forms:

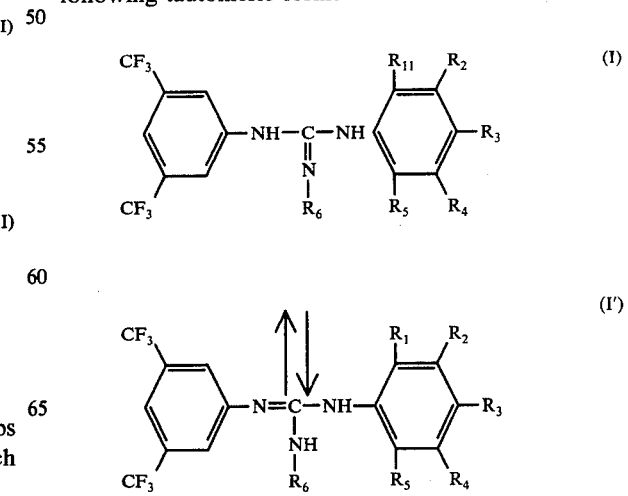

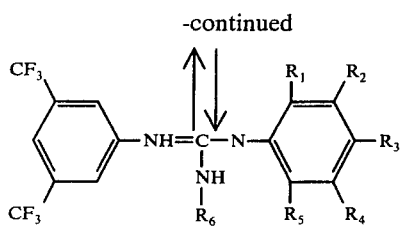

(I")

Mixtures of these three isomeric forms are obtained by the method of production described in the foregoing. Such compounds exhibit also a syn/anti isomerism.

For compounds wherein the phenyl nuclei are identically substituted, there are two conceivable tautomers (in such cases the formulae I' and I" above are equivalent). NMR-spectra show, however, that with identical substitution of the phenyl radicals there is obtained a homogeneous compound. Since the two NH-signals coincide, there exists with the greatest probability solely the structure I (syn/anti isomerism in this case not possible) and not the structure I'.

The concept of the present invention is understood to embrace the various possible isomers.

The compounds of the formula I are suitable for the control of various animal and plant pests.

These compounds exhibit in particular an excellent stomach poison action against insects, but at the same time have no contact action, or at most only a slight one, even with application of relatively high doses.

The significance of this specific stomach poison action is that compounds of the formula I act only against insects that cause damage, e.g. to plants, by eating, but do not act against for example the useful insects which live on the plants or which come into contact with the plants.

The compounds of the formula I can be used on their own or together with suitable carriers and/or additives. Suitable carriers and additives may be solid or liquid, and they correspond to the substances common in formulation practice, such as natural or regenerated substances, solvents, dispersing agents, wetting agents, adhesives, thickeners, binders and/or fertilisers.

For application, the compounds of the formula I can be processed into the form of dusts, emulsion concentrates, granulates, dispersions, sprays or solutions, the formulation of these preparations being effected in a manner commonly known in practice.

The agents according to the invention are prepared in a manner known per se by the intimate mixing and/or grinding of active substances of the formula I with suitable carriers, optionally with the addition of dispersing agents or solvents which are inert to the active substances. The active substances can be obtained and used in the following forms:

solid preparations: dusts, scattering agents, granulates (coated granulates, impregnated granulates and homogeneous granulates);

liquid preparations:
a. water-dispersible active-substance concentrates: wettable powders, pastes or emulsions;
b. solutions.

The content of active substance in the described agents is between 0.1 and 95%.

The active substances of the formula I can be formulated, for example, as follows:

Dusts

The following substances are used to produce (a) a 5% dust and (b) a 2% dust:
a. 5 parts of Active Substance, and 95 parts of talcum;
b. 2 parts of Active Substance, 1 part of highly dispersed silicic acid, and 97 parts of talcum.

The active substances are mixed and ground with the carriers.

Granulate

The following substances are used to produce a 5% granulate:
5 parts of Active Substance,
0.25 part of epichlorohydrin,
0.25 part of cetyl polyglycol ether,
3.50 parts of polyethylene glycol, and
91 parts of kaolin (particle size 0.3 - 0.8 mm).

The active substance is mixed with epichlorohydrin and the mixture is dissolved with 6 part of acetone; the polyethylene glycol and cetyl polyglycol ether are then added. The solution thus obtained is sprayed onto kaolin, and the acetone is subsequently evaporated off in vacuo.

Wettable powders

The following constituents are used to prepare (a) a 40%, (b) and (c) a 25%, and (d) a 10% wettable powder:
a. 40 parts of Active Substance, 5 parts of sodium lignin sulphonate, 1 part of sodium dibutyl-naphthalene sulphonate, and 54 parts of silicic acid;
b. 25 parts of Active Substance, 4.5 parts of calcium lignin sulphonate, 1.9 parts of Champagne chalk-/hydroxyethyl cellulose, mixture (1:1), 1.5 parts of sodium dibutyl naphthalene sulphonate, 19.5 parts of silicic acid, 19.5 parts of Champagne chalk, and 28.1 parts of kaolin;
c. 25 parts of Active Substance, 2.5 parts of isooctylphenoxy-polyoxyethylene-ethanol, 1.7 parts of Champagne chalk/hydroxyethyl cellulose mixture (1:1), 8.3 parts of sodium aluminium silicate, 16.5 parts of kieselguhr, and 46 parts of kaolin;
d. 10 parts of Active Substance, 3 parts of a mixture of the sodium salts of saturated fatty alcohol sulphates, 5 parts of naphthalenesulphonic acid/formaldehyde condensate, and 82 parts of kaolin.

The active substances are intimately mixed, in suitable mixers, with the additives; and the mixture is then ground in the appropriate mills and rollers. Wettable powders are obtained which can be diluted with water to give suspensions of any desired concentration.

Emulsifiable concentrates

The following substances are used to produce (a) a 10%, (b) a 25% and (c) a 50% emulsifiable concentrate:
a. 10 parts of Active Substance, 3.4 parts of epoxidised vegetable oil, 3.4 parts of a combination emulsifier consisting of fatty alcohol polyglycol ether and alkylarylsulphonate calcium salt, 40 parts of dimethylformamide, and 43.2 parts of xylene;
b. 25 parts of Active Substance, 2.5 parts of epoxidised vegetable oil, 10 parts of an alkylarylsulphonate/fatty alcohol polyglycol ether mixture, 5 parts of dimethylformamide, and 57.5 parts of xylene;
c. 50 parts of Active Substance, 4.2 parts of tributylphenol-polyglycol ether, 5.8 parts of calcium-dodecylbenzenesulphonate, 20 parts of cyclohexanone, and 20 parts of xylene.

It is possible to prepare from these concentrates, by dilution with water, emulsions of any desired concentration.

Sprays

The following constituents are used to produce (a) a 5% spray and (b) a 95% spray:
a. 5 parts of Active Substance, 1 part of epichlorohydrin, and 94 parts of ligroin (boiling limits 160° - 190° C); and
b. 95 parts of Active Substance, and 5 parts of epichlorohydrin.

EXAMPLE 1

Production of N-methylsuphonyl-N'-(3,4-dichlorophenyl)-N''-(3,5-bis-trifluoromethyl-phenyl)-guanidine.

Preparation of the starting material:

A. N-Methylsulphonyl-N'-(3,4-dichlorophenyl)-S-methylisothiourea:

94 g of N-methylsulphonyl-S-methylimino-thiocarbonic acid chloride (see Chem. Ber. 99, 1252 (1966)) was added, with cooling, to a solution of 81 g of 3,4-dichloroaniline (0.5 mole) and 51 g of triethylamine (0.505 mole) in 200 ml of acetonitrile, and the reaction mixture obtained was refluxed for about 1 hour. After cooling, the reaction solution was stirred into water, whereupon the crude product precipitated in the form of an oil. The oil was taken up in 300 ml of ethyl acetate and dried over sodium sulphate. After removal of the solvent by distillation in a Rotovap, there was obtained N-methylsulphonyl-N'-(3,4-dichlorophenyl)-S-methylisothiourea in the form of crystals: m.p. 122°–125° C after recrystallisation from ethyl acetate/hexane.

B. N-Methylsulphonyl-N'-(3,4-dichlorophenyl)-chloroformamidine

The N-methylsulphonyl-N'-(3,4-dichlorophenyl)-S-methylisothiourea (150 g) obtained in the manner described was suspended in 250 ml of ethyl acetate, and 45 ml of sulphonyl chloride (0.55 mole) was added dropwise to the suspension at a temperature of 50° C. The solvent as well as the formed methanesulphonyl chloride and unreacted sulphonyl chloride was distilled off in the Rotovap, and the crystallising residue was taken up in hexane. After filtration with suction, the resulting N-methylsulphonyl-N'-(3,4-dichlorophenyl)-chloroformamidine had a melting oint of 154° - 156° C.

C. Production of the final product: N-methylsulphonyl-N'-(3,4-dichlorophenyl)-N''-(3,5-bis-trifluoromethyl)-guanidine:

79.5 g of N-methylsulphonyl-N'-(3,4-dichlorophenyl)-chloroformamidine was added, with cooling, to a solution of 60.5 g of 3,5-bis-trifluoromethylaniline (0.264 mole) and 27 g of triethylamine (0.27 mole) in 200 ml of acetonitrile. The reaction mixture was heated for 2 hours, with stirring, at a temperature of 65°–70° C, and, after cooling, stirred into water, whereupon the product precipitated as an oil. This oil crystallised after a short time; the product was filtered off with suction and then dried in vacuo. The resulting N-methylsulphonyl-N'-(3,4-dichlorophenyl)-N''-(3,5-bis-trifluoromethyl-phenyl)-guanidine was finally recrystallised in ethyl acetate/hexane: m.p. 189°–193° C.

The following compounds are produced in an analogous manner:

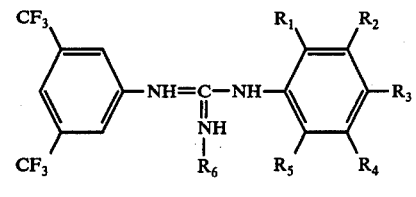

| $R_1$ | $R_2$ | $R_3$ | $R_4$ | $R_5$ | $R_6$ | Physical data |
|---|---|---|---|---|---|---|
| H | $CF_3$ | Cl | H | H | $-SO_2CH_3$ | m.p. 193–200° C |
| H | H | Cl | H | $CH_3$ | $-SO_2CH_3$ | m.p. 143–148° C |
| H | H | Cl | H | Cl | $-SO_2CH_3$ | m.p. 236–238° C |
| H | H | H | $CF_3$ | H | $-SO_2CH_3$ | m.p. 176–180° C |
| H | Cl | Cl | H | Cl | $-SO_2CH_3$ | m.p. 232–234° C |
| $CH_3$ | H | Br | H | $CH_3$ | $-SO_2CH_3$ | m.p. 188–193° C |
| H | H | Cl | $CF_3$ | H | $-SO_2CH_3$ | m.p. 160–165° C |
| H | H | H | H | H | $-SO_2CH_3$ | m.p. 148–152° C |
| $CH_3$ | H | H | H | $CH_3$ | $-SO_2CH_3$ | m.p. 175–177° C |
| H | H | Cl | H | H | $-SO_2CH_3$ | m.p. 155–160° C |
| H | $CF_3$ | H | $CF_3$ | H | $-SO_2-\langle\rangle-Cl$ | m.p. 160–162° C |
| H | H | F | $CF_3$ | H | $-SO_2CH_3$ | resin |
| H | Cl | F | H | H | $-SO_2CH_3$ | resin |
| H | H | Br | H | H | $-SO_2CH_3$ | m.p. 188–193° C |
| H | H | F | H | H | $-SO_2CH_3$ | resin |
| H | H | CN | H | H | $-SO_2CH_3$ | resin |
| H | H | $NO_2$ | H | H | $-SO_2CH_3$ | resin |
| H | H | $-C(O)-CH_3$ | H | H | $-SO_2CH_3$ | resin |
| H | H | $-O-C(O)-CH_3$ | H | H | $-SO_2CH_3$ | resin |
| H | H | Cl | H | H | $-SO_2C_2H_5$ | m.p. 167–169° C |
| H | Cl | Cl | H | H | $-SO_2C_2H_5$ | m.p. 165–167° C |
| H | Cl | Cl | H | H | $-SO_2C_4H_{9(n)}$ | m.p. 191–192° C |

-continued

| R₁ | R₂ | R₃ | R₄ | R₅ | R₆ | Physical data |
|----|----|----|----|----|----|---------------|
| H | Cl | Cl | H | H | —SO₂—C₆H₄—Cl | m.p. 198–201° C |
| H | CF₃ | OCH₃ | H | H | —SO₂—C₆H₄—Cl | m.p. 158–161° C |
| H | CF₃ | Cl | H | H | —SO₂—C₆H₄—Cl | m.p. 146–150° C |
| H | CF₃ | F | H | H | —SO₂—C₆H₄—Cl | m.p. 150–154° C |
| H | Cl | F | H | H | —SO₂—C₆H₄—Cl | m.p. 191–193° C |
| H | Cl | H | Cl | H | —SO₂—C₆H₄—Cl | m.p. 182–185° C |
| H | H | I | H | H | —SO₂—C₆H₄—Cl | m.p. 203–205° C |
| Cl | H | Cl | H | H | —SO₂—C₆H₄—CH₃ | m.p. 142–144° C |
| H | H | Br | H | H | —SO₂—C₆H₄—Cl | m.p. 192–196° C |
| H | Cl | H | H | Cl | —SO₂CH₃ | m.p. 186–188° C |
| Cl | Cl | H | H | H | —SO₂CH₃ | m.p. 180–182° C |
| H | OCH₃ | H | OCH₃ | H | —SO₂CH₃ | m.p. 143–145° C |

EXAMPLE 2

Young mallow plants of the species Malv silvestris were completely wetted by immersion in the respective test solutions, and subsequently dried in a greenhouse. The solutions were produced from a 25% wettable powder of the test preparations, and applied at concentrations of 800, 400, 200 and 100 ppm of active substance to the mallow plants.

After drying of the coatings, 1 mallow leaf, which had been protected from premature withering by the placing of a moist cottonwool pad around the petiole, was infested in each case with 5 L₃-stages of the test species, namely, Spodoptera littoralis, Heliothis armigera and Heliothis virescens. Plastics Petri dishes were used as containers.

A percentage evaluation of the attained destruction of the larvae was made after 1, 2 and 5 days. If the leaf became completely eaten by the larvae with little insecticidal action, then they received a new leaf from the same treated test plant, and so on until the test was completed. Where, however, there occurred a 100% destruction before reaching the end of the test after 5 days, the identical plant material of the initially treated test plant was infested with 5 new larvae of the L₃-stage. This experimental arrangement thus provided an evaluation of the residual effect of the ageing insecticidal coatings.

The compounds according to Example 1 exhibited in the above test a good stomach-poison action against caterpillars of Spodoptera littoralis, Heliothis armigera and Heliothis virescens.

EXAMPLE 3

Stomach poison action

Five young bean plants (Phaseolus vulgaris) were treated, in a manner analogous to that described in Example 2, by immersion in test solutions of the same dilution series. After drying and infestation with the test insects (Epilachna varivestis: L-4-stage), there was placed over each plant a cellophane bag, which was secured to the pot with a rubber band, and thus prevented the test insects from migrating away from the treated plants. An evaluation was carried out after 2 and 5 days.

The compounds according to Example 1 were effective in the above test against larvae of Epilachna varivestis.

We claim:

1. A N,N'-diphenyl-guanidine derivative of the formula

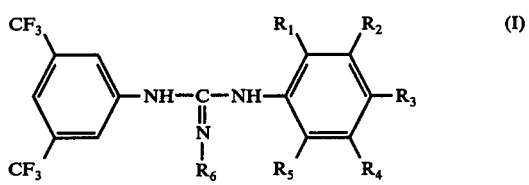

wherein
   R₁, R₂, R₃, R₄ and R₅ each represent hydrogen, halogen, C₁-C₅-alkyl, C₁-C₅-halogenoalkyl, C₁-C₅-alkoxy, (C₁-C₅-alkyl)-carbonyl, (C₁-C₅-alkoxy)-carbonyl, cyano or nitro, and
   R₆ represents C₁-C₅-alkylsulphonyl, phenylsulphonyl or phenylsulphonyl substituted on the phenyl ring by halogen, C₁-C₅ alkyl, C₁-C₅ alkoxy, trifluoromethyl, nitro, amino or cyano.

2. A compound according to claim 1, wherein R₁, R₂, R₃, R₄ and R₅ each represent hydrogen, chlorine or trifluoromethyl, and R₆ represents methylsulphonyl, ethylsulphonyl or 4-chlorophenylsulphonyl.

3. The compound according to claim 2 of the formula

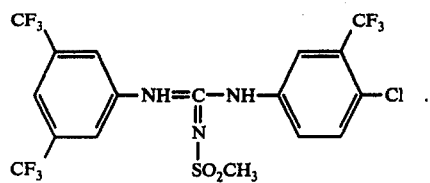

4. The compound according to claim 2 of the formula

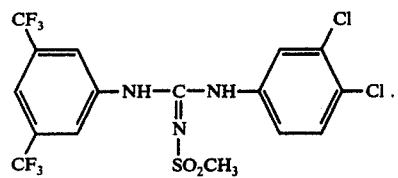

5. The compound according to claim 2 of the formula

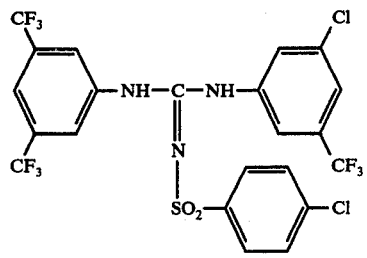

6. The compound according to claim 2 of the formula

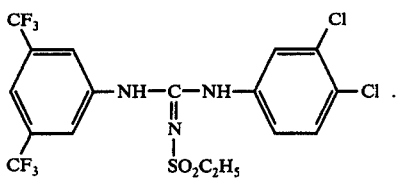

7. An insecticidal composition comprising as active ingredient an insecticidally effective amount of a compound according to claim 1, together with a suitable carrier therefor.

8. A method for the control of insects comprising applying to the locus thereof an insecticidally effective amount of a compound according to claim 1.

* * * * *